(12) United States Patent
Hassler et al.

(10) Patent No.: US 7,285,104 B2
(45) Date of Patent: Oct. 23, 2007

(54) ORTHOTIC DEVICE FOR THE ANKLE JOINT

(75) Inventors: Andreas Hassler, Rohrdorf (DE); Gero Hopmann, Neubiberg (DE)

(73) Assignee: OPED AG, Steinhausen (CH)

( * ) Notice: Subject to any disclaimer, the term of this patent is extended or adjusted under 35 U.S.C. 154(b) by 26 days.

(21) Appl. No.: 10/542,705

(22) PCT Filed: Dec. 15, 2003

(86) PCT No.: PCT/EP03/14251

§ 371 (c)(1),
(2), (4) Date: Jan. 5, 2006

(87) PCT Pub. No.: WO2004/066889

PCT Pub. Date: Aug. 12, 2004

(65) Prior Publication Data

US 2006/0142682 A1   Jun. 29, 2006

(30) Foreign Application Priority Data

Jan. 28, 2003   (DE) ............................... 103 03 326

(51) Int. Cl.
*A61F 5/00* (2006.01)
(52) U.S. Cl. .......................................... 602/27; 602/65
(58) Field of Classification Search .................... 602/5, 602/14, 20, 23, 27–29
See application file for complete search history.

(56) References Cited

U.S. PATENT DOCUMENTS 5,527,269 A   6/1996   Reithofer
6,053,884 A   4/2000   Peters

FOREIGN PATENT DOCUMENTS

| | | |
|---|---|---|
| DE | 93 19 990 U1 | 12/1993 |
| DE | 44 18 855 A1 | 5/1994 |
| DE | 94 08 537 U1 | 5/1994 |
| DE | 196 38 683 A1 | 9/1996 |
| EP | 0 454 186 A2 | 6/1988 |
| EP | 0 770 368 A1 | 10/1996 |
| WO | WO 95/31951 | 5/1995 |
| WO | WO 95/32692 | 5/1995 |
| WO | WO 98/08470 A1 | 8/1997 |
| WO | WO 98/11851 | 9/1997 |
| WO | WO 02/051343 | 7/2002 |

OTHER PUBLICATIONS

International Search Report dated Apr. 16, 2004.

*Primary Examiner*—Kim M. Lewis
(74) *Attorney, Agent, or Firm*—Reed Smith LLP; Stanley P. Fisher, Esq.; Juan Carlos A. Marquez, Esq.

(57) ABSTRACT

Orthotic device for the ankle joint for external fixation of the ankle joint, with a median supporting shell and a lateral supporting shell forming a shell composite by means of a connecting device is provided. The shell composite is provided with a lining for form-fitting contact of the orthotic device for the ankle joint. By the orthotic device for the ankle joint, the joining device has an elastic connecting clasp with a tibial clasp opening which secures the supporting shells in their relative arrangement so that their positions are variable.

28 Claims, 5 Drawing Sheets

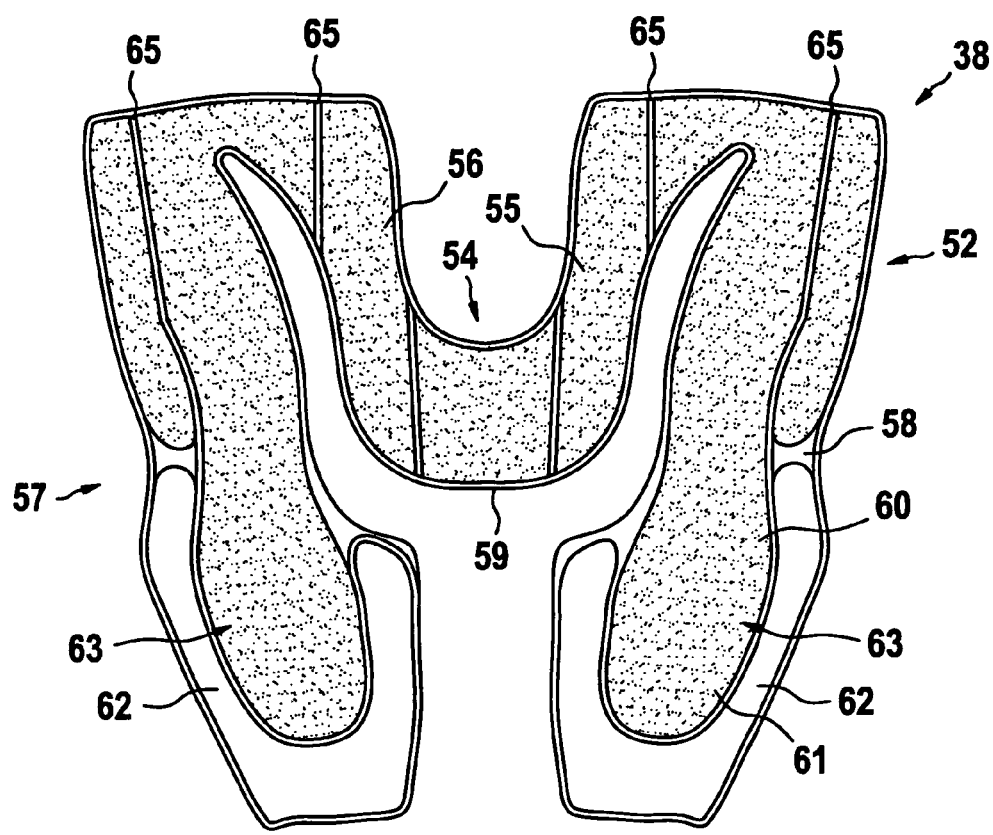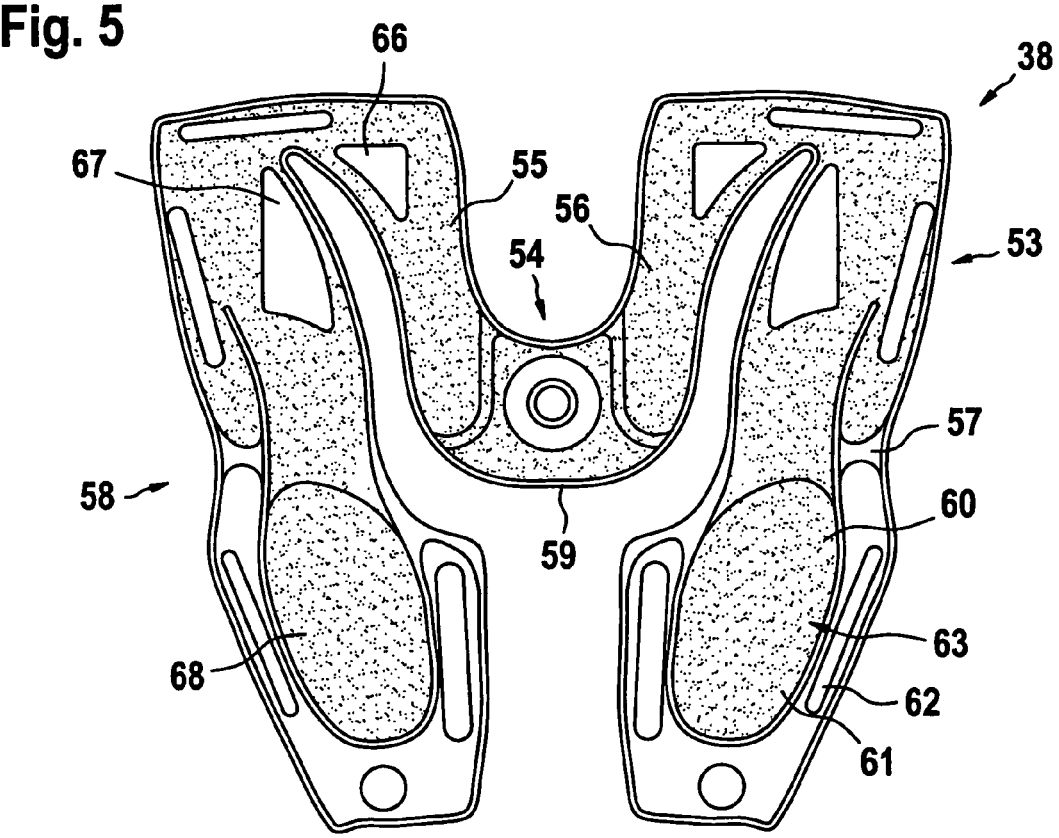

ORTHOTIC DEVICE FOR THE ANKLE JOINT

FIELD OF THE INVENTION

Figure 1:
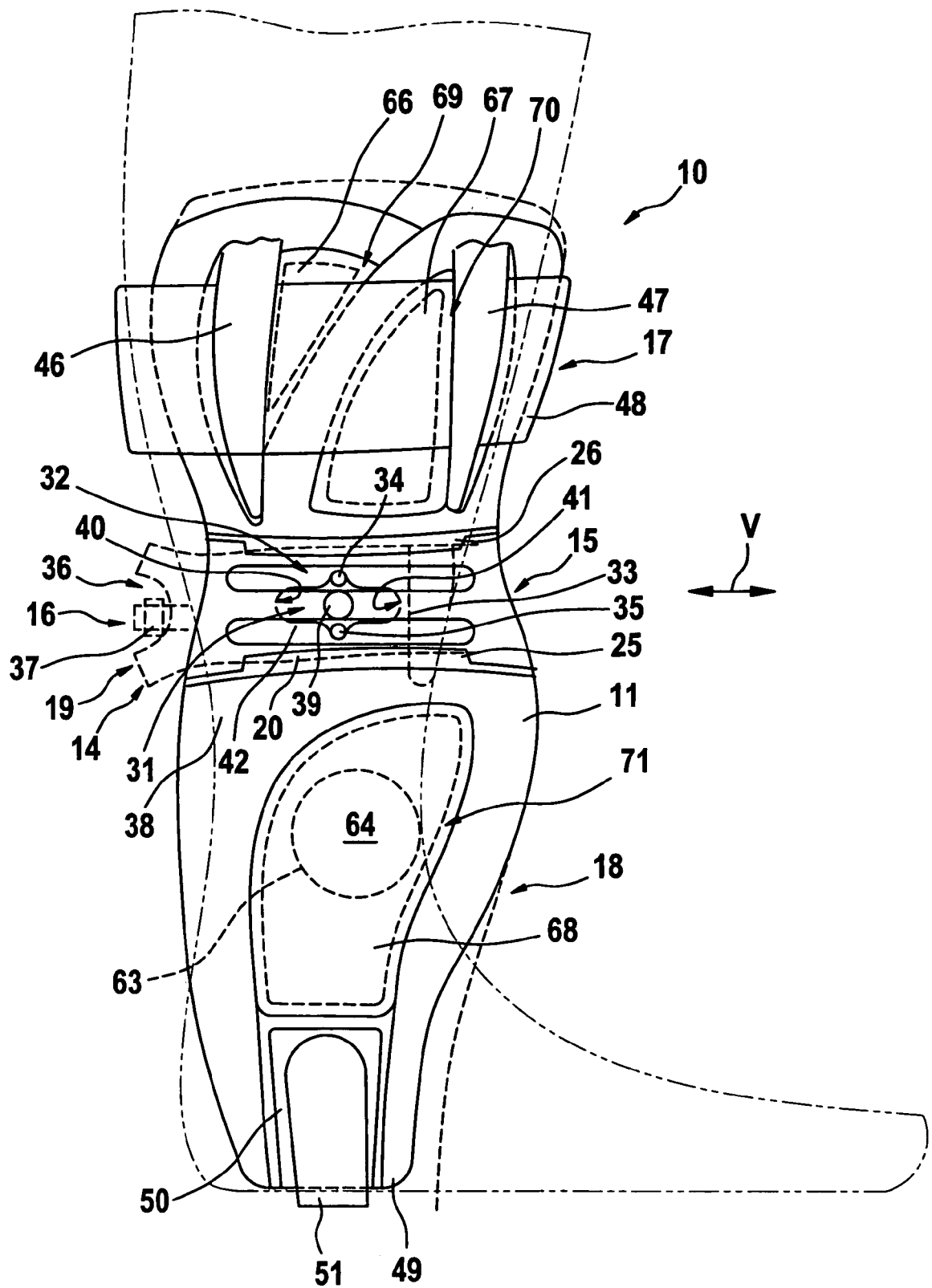

The present invention relates to an orthotic device for the ankle joint for external fixation of the ankle joint using a median supporting shell and a lateral supporting shell which form a shell composite by means of a joining device, said shell composite being provided with a lining for form-fitting contact with the orthotic device for the ankle joint.

BACKGROUND OF THE INVENTION

Orthotic devices for the ankle joint of the type defined above are used in particular for treatment of sprained ligaments in the area of the ankle joint or after surgical procedures in the area of the ankle joint, in particular as part of an early functional treatment.

Regardless of the specific indication, accurate seating of the orthotic device for the ankle joint in a manner that is reproducible with the greatest possible precision is essential for optimum functioning of the orthotic device for the ankle joint. In addition, an orthotic device for the ankle joint should be as easy as possible for the patient himself to handle—in particular if it is used as part of an early functional therapy—to be able to achieve the greatest possible degree of acceptance and thus frequent use of the orthotic device for the ankle joint accordingly.

SUMMARY OF THE INVENTION

Therefore the object of the present invention is to propose an orthotic device for the ankle joint that will permit positioning of the orthotic device for the ankle joint in a manner that is reproducible with the greatest possible precision, with an optimum supporting effect and with the simplest possible handling.

With the inventive orthotic device for the ankle joint, the composite device has an elastic connecting clasp with a tibial clasp opening that secures the supporting shells variably in their relative arrangement.

Before the orthotic device for the ankle joint is applied the supporting shells are already arranged in defined relative positions by means of the connecting rod which is designed to be elastic. When the device is applied, which is done by pushing the orthotic device for the ankle joint in a fibular direction onto the ankle joint, the elastic connecting rod allows the orthotic device for the ankle joint to be spread apart with a subsequent conversion of the supporting shells into a basic configuration of the orthotic device for the ankle joint that is essentially in contact with the talocrural area on both sides due to the elastic restoring forces. In addition, the variable relative positioning of the supporting shells in relation to one another permits an individual adjustment of the positioning of the supporting shells so that the seating of the orthotic device for the ankle joint can be adapted easily to the particular anatomical conditions.

An especially convenient adjustment of the relative positioning of the supporting shells is made possible if the connecting clasp is variable in its relative position with respect to the median supporting shell and also in its relative position with respect to the lateral supporting shell according to a preferred embodiment.

The change in relative positioning is especially easy to accomplish and is also easily reproducible when a catch connection device is provided for connecting the connecting clasp to at least one supporting shell in a connecting area of the supporting shell.

Ease of operation of the catch connection device by pressing on the connecting clasp on the heel end is made possible if the catch connection device is provided with a guidance device arranged across the longitudinal extent of the supporting shells, permitting a catch engagement of the clasp legs of the connecting clasp with a catch device arranged on the supporting shells in several relative positions along a guidance path defined by the guidance device.

According to a design of the orthotic device for the ankle joint that is especially easy to implement from the point of view of manufacturing technology and also facilitates the most rigid possible design of the supporting shells, the guidance device has a guidance web arrangement with two guidance webs for intermediate accommodation of a clasp leg of the connecting clasp, whereby the guidance webs are provided in at least some sections with a protrusion covering an edge area of the clasp leg.

If the guidance device has a stop device for limiting a relative movement of the connecting clasp along the guidance path, then the extreme positions of the relative positioning of the supporting shells can be pre-selected in any case so as to permit contact with the orthotic device for the ankle joint independently of the set relative positions.

If a stop is provided between the guidance webs of the supporting shells for the design of the stop mechanism and this stop cooperates with two transverse edges of a stop groove designed in the clasp legs of the connecting clasp, then it is possible to use the relative position of the stop in the stop groove simultaneously as a display device for the relative positioning of the supporting shells in relation to one another to facilitate the reproducibility of a position of the orthotic device for the ankle joint, once said position has been selected, even when the orthotic device is applied again.

If the supporting shells are provided with a recess for an anklebone area of the lining in a talocrural area below the connecting area, then this permits an especially good adaptation of the shape of the orthotic device for the ankle joint to the actual ankle joint area on the one hand while on the other hand the positioning of the orthotic device for the ankle joint is facilitated for optimum seating of same in the talocrural area. In addition, this permits engagement of the lining in the supporting shells, thus resulting in fixation of the seating of the lining in the supporting shells.

A further improvement in the fixation of the lining in the supporting shells is possible if the supporting shells are provided with a recess for a mold protrusion in the lining in the calf area above the connecting area.

In the area of the connecting clasp, fixation of the relative positions between the lining and the supporting shell composite may be accomplished by providing the connecting clasp with a recess for passing a mold protrusion in the lining through it.

If the lining is designed as a molded cushion that can be filled with air or evacuated, then the molded protrusion may be formed by a valve device.

If the elastic restoring forces of the connecting clasp that have already been mentioned above are not sufficient to produce the required supporting effect of the orthotic device for the ankle joint, then it is possible to provide the connecting clasp with a locking device which passes over the clasp opening in the area of the tibia for connecting the legs of the clasp in a manner guaranteeing tensile strength.

Furthermore, it has also proven to be advantageous to provide a web strip which can be elongated beneath the sole of the foot for connecting the longitudinal ends of the supporting shells in the area of the sole of the foot in a manner that guarantees tensile strength, in order to prevent in particular an unwanted upward movement—e.g., induced by walking movements—of the orthotic device for the ankle joint.

If both of the longitudinal ends of the web strip are attached to the supporting shells by a hook and loop fastener (i.e., VELCRO®-type) closure, then it is possible to adjust the effective length of the web strip as desired by the patient in a particularly convenient manner using either the right or left hand.

In addition, it is also possible to provide a thigh strip for joining the thigh areas of the supporting shells in a manner that guarantees tensile strength in order to achieve a particularly secure seating of the orthotic device for the ankle joint by stabilizing the supporting shell composite in the thigh area as well.

A further contribution to secure positioning of the orthotic device for the ankle joint in the talocrural area is achieved by designing the lining as a vacuum cushion with a molded body filling arranged in a cushion cover and with a padded edge having a fluid filling that is designed in one piece with the ankle area of the vacuum cushion but is independent of it in fluid terms.

It has proven to be especially advantageous for the positioning of the lining in the supporting shell composite if the lining has three cushion parts that are joined together in fluid terms, namely a U-shaped connecting part with the valve device arranged in a base area of the connecting part and with two shell parts each running in the longitudinal direction of the legs of the connecting part and departing from the free ends of the legs.

DETAILED DESCRIPTION OF THE INVENTION

A preferred embodiment of the orthotic device for the ankle joint is explained in greater detail below with reference to the drawings.

Figure 2:
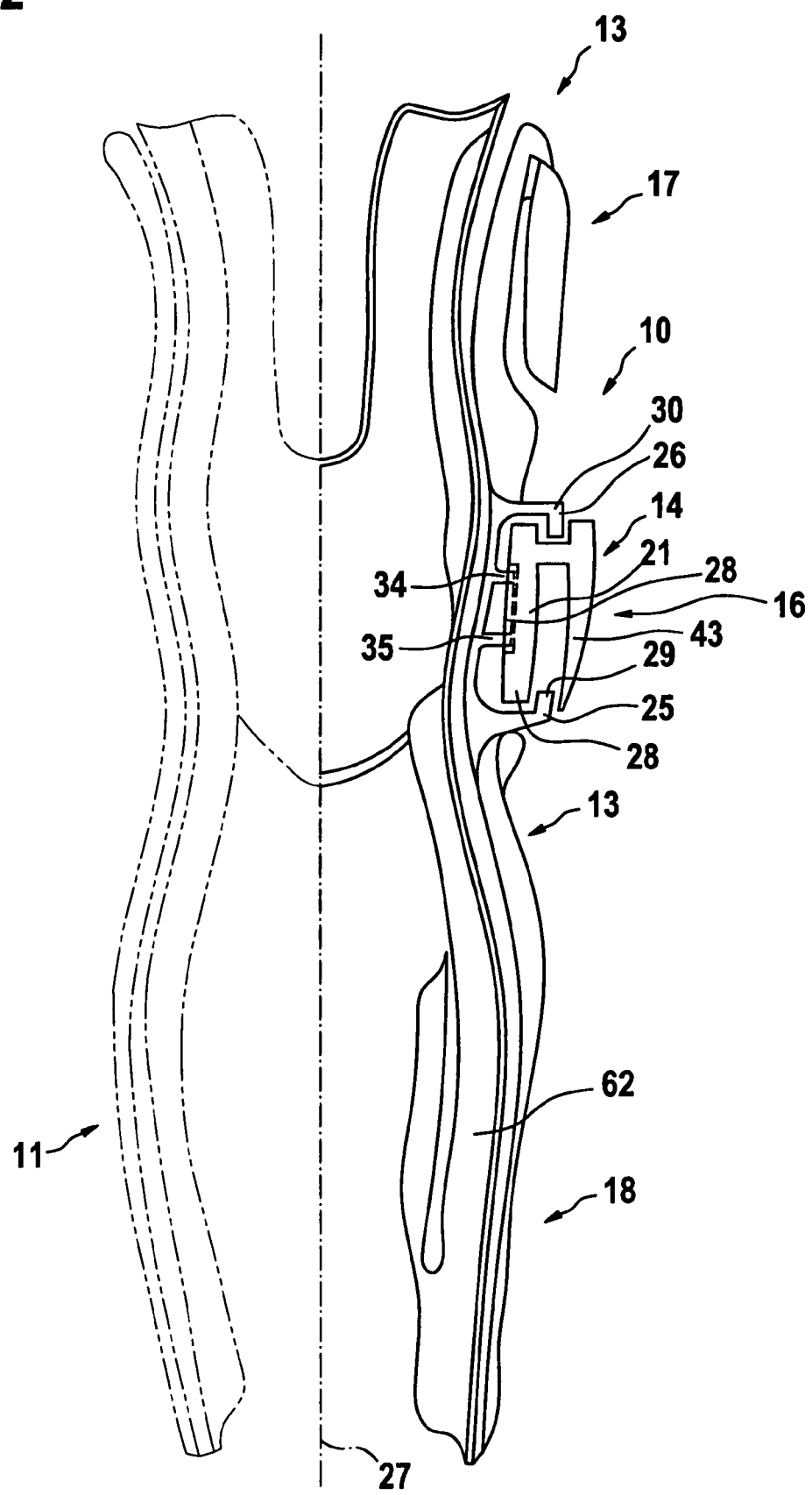
Figure 3:
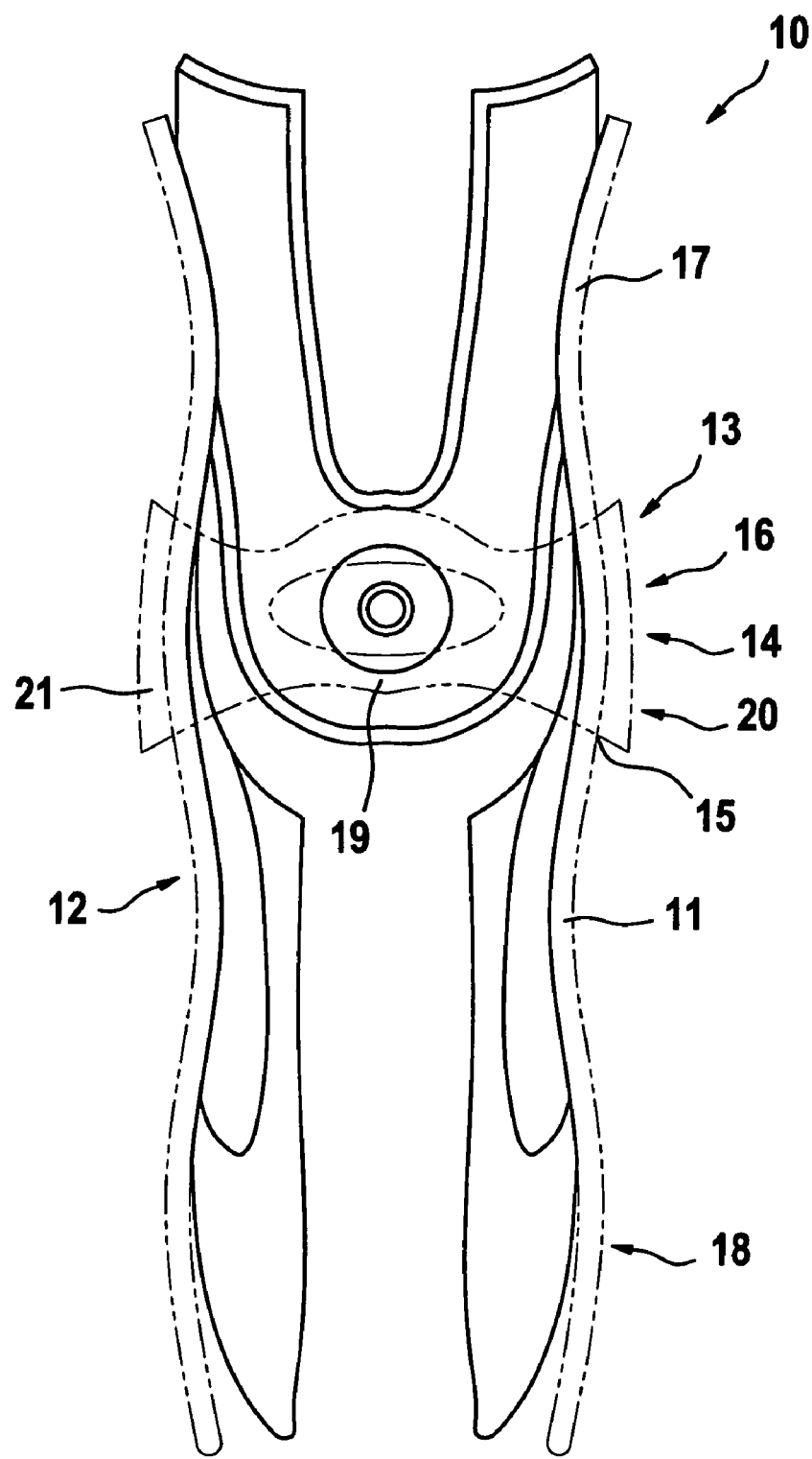
Figure 6:
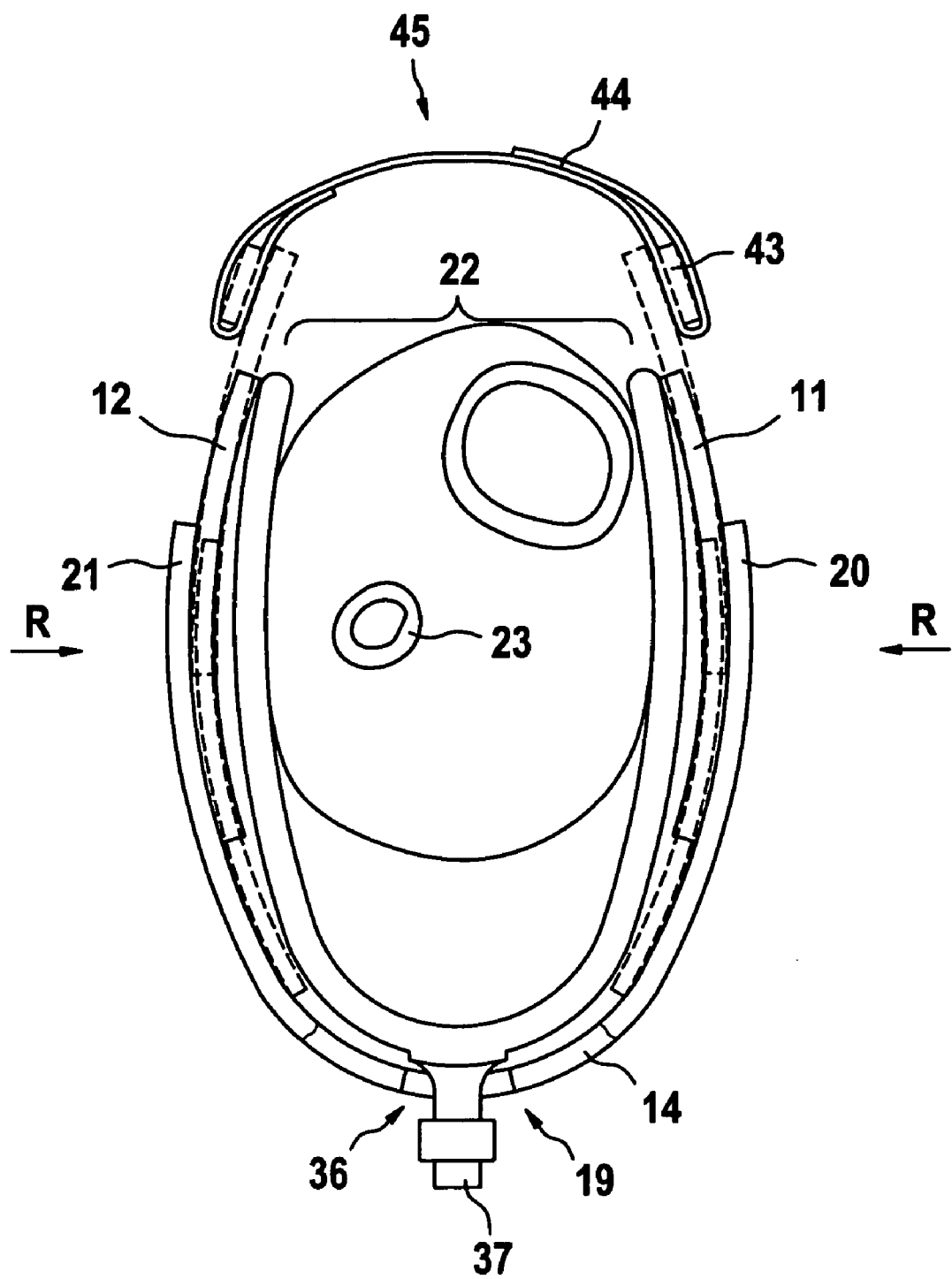

They show:

FIG. 1 an orthotic device for the ankle joint having a lining in a side view with a diagram of a median supporting shell and a connecting clasp which joins the median supporting shell to the lateral supporting shell (not visible in the drawing);

FIG. 2 a front view of the orthotic device for the ankle joint as seen from the shin side;

FIG. 3 a rear view of the orthotic device for the ankle joint showing the connecting clasp joining the supporting shells together;

FIG. 4 a diagram of the lower leg contact side of the lining which spreads out in the plane;

FIG. 5 a diagram of the supporting shell contact side of the lining spread out in the plane;

FIG. 6 a diagram of the extreme positions of the supporting shells.

From a combined view of FIGS. 1, 2 and 3, the design of an orthotic device 10 for the ankle joint is shown clearly with a connecting clasp 14 which joins a median supporting shell 11 and a lateral supporting shell 12 to form a supporting shell composite 13. The median supporting shell 11 and the lateral supporting shell 12 are designed identically with regard to the features described below.

As FIG. 1 shows, the median supporting shell 11 is composed essentially of three sections, namely a connecting area 15 which serves to form a connecting device 16 with the cooperation of the connecting clasp 14, a thigh area 17 formed above the connecting area 15 and an talocrural area 18 formed beneath the connecting area 15.

As shown in particular by a combination of FIGS. 1 and 3, the connecting clasp 14 is designed essentially in a U shape, with its clasp legs 20, 21, emerging from a clasp base 19, each wrapping around a respective supporting shell 11, 12. To permit fixation of the clasp legs 20, 21 on the supporting shells 11 and/or 12 such that the fixation can be varied in the longitudinal direction of the clasp legs 20, 21 and/or across the longitudinal extent of the supporting shells 11, 12, the composite device 16 is designed as a catch connection in the present exemplary embodiment, permitting a fixed relative position of the connecting clasp 14 and/or the clasp legs 20, 21 with respect to the supporting shells 11, 12.

To illustrate the possible relative positions, FIG. 6 shows the extreme positions of the supporting shells 11, 12 defining the displacement path of the supporting shells 11, 12 with respect to the clasp legs 20, 21; these extreme positions are indicated by a dotted line of the cross-sectional contours of the supporting shells 11, 12.

The connecting clasp 14 in the present exemplary embodiment is made of an elastic plastic such as polyamide so that spreading the clasp legs 20, 21 apart induces corresponding elastic restoring forces which are indicated by the arrows R in FIG. 6 and cause the supporting shells 11, 12 to press against the lower leg.

Furthermore, it is clear that spreading the clasp legs 20, 21 permits widening of a clasp opening 22 which is bordered by the free ends of the clasp legs 20, 21 and thus permits unhindered positioning of the orthotic device 10 for the ankle joint and/or the supporting shell composite 13 formed from the supporting shells 11, 12.

As shown in FIGS. 1 and 2 in particular, the composite device 16 includes a guidance web arrangement 24 provided in the connecting area 15 of the supporting shells 11, 12 and having two guidance webs 25, 26 that are arranged parallel to one another and run across the longitudinal direction of the supporting shell 11. Between the guidance webs 25, 26, a clasp leg 20 and/or 21 is inserted and is gripped in at least some sections by protrusions designed as holding webs 29, 30. The holding webs 29, 30 are of such dimensions that the clasp legs made of an elastic material can be clipped behind the holding webs 29, 30 so that a connection of the connecting clasp 14 to the supporting shells 11, 12 can be established easily and released easily whereby at the same time the connection established between the connecting clasp 14 and the supporting shells 11, 12 is secure enough to function satisfactorily during use of the orthotic device for the ankle joint, i.e., to permit satisfactory fixation of the supporting shells 11, 12 in their relative positions by the connecting clasp 14.

As FIG. 1 shows, a catch device 32 consisting of two catch noses 34, 35 arranged laterally on an elastic web 33 of the connecting area 15 is provided on the supporting shell 11 to form a catch engagement device 31 between the connecting area 15 of the supporting shell 11 and the clasp leg 20 of the connecting clasp 14. The catch noses 34, 35 engage in catch grooves 28 (FIG. 2) running across the direction of displacement V (FIG. 1) and provided on a supporting shell contact side 36 of the clasp leg 20 or 21, these catch grooves preferably being arranged so they are equidistant and permit defined catch positions of the connecting clasp 14 and/or the clasp leg 20, 21 with respect to the supporting shell 11, 12.

As also indicated by FIGS. 1 and 6, the clasp base 19 of the connecting clasp 14 is provided with a through-opening 36 which serves to pass a valve device 37 in the lining which is designed in the present case as an evacuable molded cushion 38. The arrangement of the valve device 37 in the area of the through-opening 36 in the catch base 19 ensures not only a protected arrangement of the valve device 37 but also a definite positioning of the valve device 37, permitting easy access to the valve device 37 for venting and/or evacuating the molded cushion 38. In addition, the arrangement of the valve device 37 in the area of the through-opening 36 also makes it possible to secure the position of the molded cushion 38 with respect to the supporting shell composite 13 of the orthotic device 10 for the ankle joint.

To develop defined end stops between the connecting clasp 14 and the supporting shells 11, 12 which border the displacement path V in both directions, the supporting shell 11 and/or 12 is provided with a stopping nub 39 (FIG. 1) on the web 33 of the connecting area 15, said stopping nub coming to rest against cross edges 40, 41 of a stop groove 42 formed in the clasp leg 20 and/or 21 in the end positions of the displacement path V. In addition, the relative position of the stop nub 39 which is visible from the outside with respect to the stop groove 42 may be used as a display device which facilitates reproducibility of a selected relative position between the connecting clasp 14 and the supporting shells 11, 12.

1. In particular for the case when the pressing force of the supporting shells 11, 12 produced by the abovementioned restoring forces against the lower leg of the patient is not sufficient to achieve a secure supporting effect, tension straps 43 (FIG. 6) are provided on the free ends of the clasp legs 20, 21; loops of a tension belt 45 secured by hook and loop fastener (i.e., VELCRO®-type)-type fasteners 44, for example, can be wrapped around these straps in order to increase the pressure of the supporting shells 20, 21 against the lower leg by reducing the size of the clasp openings 22.

In the calf area 17 of the supporting shell 11 and/or 12 (FIG. 1), two guidance straps 46, 47 are provided in the present exemplary embodiment; these straps permit a defined wrap guidance of a calf tension belt 48 around the lower leg with intermediate accommodation of the calf areas 17 of the supporting shells 11, 12 in the manner of belt loops.

Fastening areas 50 are provided on the lower longitudinal ends 49 (FIG. 1) of the supporting shells 11, 12, preferably designed as a hook area which can be contacted with a loop area of a web strip 51 extending between the fastening areas 50 of the two supporting shells 11, 12 over the sole of the foot and thus preventing the orthotic device 10 for the ankle joint from slipping up.

FIGS. 4 and 5 show a top view of the molded cushion 38 which is spread out in a plane; FIG. 4 shows a lower leg contact side 52 and FIG. 5 shows a shell contact side 53. The molded cushion 38 has three interconnected parts, namely a central U-shaped connecting part 54 and two shell parts 57, 58, branching off from connecting part legs 55, 56 at the upper end and extending approximately in the longitudinal direction of the connecting part legs 55, 56 to beneath a connecting part base 59. The two shell parts 57, 58 of the molded cushion 38 are pneumatically connected to the connecting part 54 and, like the latter, have a molded body filling 60 of individual molded bodies 61. The shell parts 57, 58 each have a U-shaped cushioned edge 62 in an area located beneath the connecting part 54, filled with an air volume and separated from the other areas of the molded cushion in fluid terms. The cushioned edge 62 borders an ankle area 63 of the shell parts 57, 58 coming to lie on the ankle 64 of the foot when the orthotic device 10 for the ankle joint is applied, as illustrated in FIG. 1.

As shown in particular in the diagram in FIG. 2, the cushioned edge 62 forms an air cushion but also secures the relative position of the supporting shells 11, 12 in the ankle area due to the accommodation of the ankle 64 surrounded by the cushioned edge 62 (FIG. 1).

As FIG. 4 also shows, hinge areas 65 are provided on the lower leg contact side 52 of the molded cushion 38 with constrictions of the cross section being designed in the molded cushion 38, which thereby on the one hand permit undisturbed fluid passage but on the other hand areas of the cross section with a reduced diameter are allowed for definition of a hinge function. On the basis of the hinge areas, an adaptation of the molded cushion 38 to the supporting shell composite 13 and/or to the contour of the lower leg is facilitated.

As FIG. 5 shows, elevated form-fitting bodies 66, 67, 68 are formed on the shell contact side 53 of the molded cushion 38 in both the calf area of the molded cushion 38 as well as in the ankle area 63; these bodies are elevated with respect to the plane of the shell contact side 53 and are formed by a corresponding contouring of the shell contact side 53, and they are also provided with a molded body filling 60 exactly like the surrounding areas of the molded body 38. As FIG. 1 shows, the form-fitting bodies 66 and 67 engage in form-fitting recesses 69, 70 which are arranged in the calf area 17 of the supporting shells 11, 12. The form-fitting body 68 engages in a corresponding form-fitting recess 71 provided in the talocrural area 18 of the supporting shells 11, 12. This secures the relative position of the molded cushion 38 with respect to the supporting shells 11, 12 on the one hand while on the other hand creating areas in which an adaptation of the molded cushion 38 is possible due to evacuation in the covered areas of the lower leg and/or ankle joint without any hindrance on deformation due to the supporting shells 11, 12.

The invention claimed is:

1. An orthotic device for the ankle joint for external fixation of the ankle joint, having a median supporting shell and a lateral supporting shell which form, by means of a joining device, a shell composite which is provided with a lining for form-fitting contact with the orthotic device for the ankle joint, characterized in that the composite device has an elastic connecting clasp with a tibial clasp opening which secures the supporting shells in their relative arrangement to one another in a variable manner.

2. The orthotic device for the ankle joint according to claim 1, characterized in that the connecting clasp is variable in its relative position with respect to the median supporting shell as well as in its relative position with respect to the lateral supporting shell.

3. The orthotic device for the ankle joint according to claim 2, characterized in that for joining the connecting clasp to at least one supporting shell in a connecting area of the supporting shell a catch engagement device is provided.

4. The orthotic device for the ankle joint according to claim 3, characterized in that the catch engagement device is provided with a guidance device arranged across the longitudinal extent of the supporting shells, permitting a locking engagement of clasp legs of the connecting clasp with a catch device arranged on the supporting shells in several relative positions along a guidance path defined by the guidance device.

5. The orthotic device for the ankle joint according to claim 4, characterized in that
the guidance device has a guidance web arrangement with two guidance webs for intermediate accommodation of a clasp leg of the connecting clasp, whereby the guidance webs are provided in at least some sections with a protrusion which covers an edge area of the clasp leg.

6. The orthotic device for the ankle joint according to claim 5, characterized in that
the guidance device is provided with a stop device for limiting a relative movement of the connecting clasp along the guidance path.

7. The orthotic device for the ankle joint according to claim 6, characterized in that
to form the stop device between the guidance webs of the supporting shells, a stop is provided, cooperating with two cross edges of a stop groove provided in the clasp legs.

8. The orthotic device for the ankle joint according to claim 4, characterized in that
the guidance device is provided with a stop device for limiting a relative movement of the connecting clasp along the guidance path.

9. The orthotic device for the ankle joint according to claim 8, characterized in that
to form the stop device between the guidance webs of the supporting shells, a stop is provided, cooperating with two cross edges of a stop groove provided in the clasp legs.

10. The orthotic device for the ankle joint according to claim 3, characterized in that
the supporting shells are provided with a recess for an ankle area of the lining in a talocrural area below the connecting area.

11. The orthotic device for the ankle joint according to claim 3, characterized in that
the supporting shells are provided with a recess for a molded protrusion of the lining in a calf area above the connecting area.

12. The orthotic device for the ankle joint according to claim 1, characterized in that
for joining the connecting clasp to at least one supporting shell in a connecting area of the supporting shell a catch engagement device is provided.

13. The orthotic device for the ankle joint according to claim 12, characterized in that
the catch engagement device is provided with a guidance device arranged across the longitudinal extent of the supporting shells, permitting a locking engagement of clasp legs of the connecting clasp with a catch device arranged on the supporting shells in several relative positions along a guidance path defined by the guidance device.

14. The orthotic device for the ankle joint according to claim 13, characterized in that
the guidance device has a guidance web arrangement with two guidance webs for intermediate accommodation of a clasp leg of the connecting clasp, whereby the guidance webs are provided in at least some sections with a protrusion which covers an edge area of the clasp leg.

15. The orthotic device for the ankle joint according to claim 14, characterized in that
the guidance device is provided with a stop device for limiting a relative movement of the connecting clasp along the guidance path.

16. The orthotic device for the ankle joint according to claim 15, characterized in that
to form the stop device between the guidance webs of the supporting shells, a stop is provided, cooperating with two cross edges of a stop groove provided in the clasp legs.

17. The orthotic device for the ankle joint according to claim 13, characterized in that
the guidance device is provided with a stop device for limiting a relative movement of the connecting clasp along the guidance path.

18. The orthotic device for the ankle joint according to claim 17, characterized in that
to form the stop device between the guidance webs of the supporting shells, a stop is provided, cooperating with two cross edges of a stop groove provided in the clasp legs.

19. The orthotic device for the ankle joint according to claim 13, characterized in that
the connecting clasp has a locking device for connecting the clasp legs over the tibial clasp opening in a connection that guarantees tensile strength.

20. The orthotic device for the ankle joint according to claim 19, characterized in that
a web band is provided for connecting the longitudinal ends of the supporting shells that are in the area of the sole of the foot in a connection that guarantees tensile strength.

21. The orthotic device for the ankle joint according to claim 20, characterized in that
the two longitudinal ends of the web band are each connected to the supporting shells by a hook and loop fastener connection.

22. The orthotic device for the ankle joint according to claim 12, characterized in that
the supporting shells are provided with a recess for an ankle area of the lining in a talocrural area below the connecting area.

23. The orthotic device for the ankle joint according to claim 12, characterized in that
the supporting shells are provided with a recess for a molded protrusion of the lining in a calf area above the connecting area.

24. The orthotic device for the ankle joint according to claim 23, characterized in that
a calf band is provided for a connection of the calf areas of the supporting shells such that the connection guarantees tensile strength.

25. The orthotic device for the ankle joint according to claim 1, characterized in that
the connecting clasp is provided with a recess for allowing a mold protrusion of the lining to pass through.

26. The orthotic device for the ankle joint according to claim 25, characterized in that
the lining is designed as a molded cushion that can be filled with air or evacuated with a valve device which forms the mold protrusion.

27. The orthotic device for the ankle joint according to claim 1 characterized in that
the lining is designed as a vacuum cushion with a molded body filling arranged in a cushion cover and a padded edge, which is designed in one piece with an ankle area of the vacuum cushion independently in fluid terms and has a fluid filling.

28. The orthotic device for the ankle joint according to claim 1, characterized in that the lining has three cushion parts joined together in fluid terms, namely a U-shaped connecting part with a valve device arranged in a base area of the connecting part and with two shell parts branching off from the free ends of the legs, each running in the longitudinal direction of the legs of the connecting part.

* * * * *